United States Patent [19]

Block et al.

[11] Patent Number: 4,582,809

[45] Date of Patent: Apr. 15, 1986

[54] APPARATUS INCLUDING OPTICAL FIBER FOR FLUORESCENCE IMMUNOASSAY

[75] Inventors: Myron J. Block, 334 N. Main St., North Salem, N.H. 03073; Tomas B. Hirschfeld, Livermore, Calif.

[73] Assignee: Myron J. Block, North Salem, N.H.

[21] Appl. No.: 406,324

[22] Filed: Aug. 9, 1982

Related U.S. Application Data

[63] Continuation-in-part of Ser. No. 388,193, Jun. 14, 1982, abandoned.

[51] Int. Cl.⁴ .................. G01N 33/53; G01N 33/533; G01N 33/552; G01N 21/64
[52] U.S. Cl. .................................... 436/527; 250/227; 250/302; 250/365; 356/73.1; 356/445; 422/57; 422/68; 436/172; 436/805
[58] Field of Search .................... 436/527, 805, 172; 422/56, 57, 68; 250/227, 302, 365; 356/73.1, 445

[56] References Cited

U.S. PATENT DOCUMENTS

| | | | |
|---|---|---|---|
| 3,939,350 | 2/1976 | Kronick | 250/302 X |
| 3,998,591 | 12/1976 | Eckfeldt | 422/86 X |
| 4,050,895 | 9/1977 | Hardy | 436/805 X |
| 4,106,909 | 8/1978 | David | 436/100 X |
| 4,133,639 | 1/1979 | Harte | 422/57 X |
| 4,321,057 | 3/1982 | Buckles | 422/58 X |
| 4,341,957 | 7/1982 | Wieder | 250/365 X |
| 4,368,047 | 1/1983 | Andrade | 436/805 X |
| 4,399,099 | 8/1983 | Buckles | 436/805 X |
| 4,447,546 | 5/1984 | Hirschfeld | 436/805 X |

Primary Examiner—Sidney Marantz
Attorney, Agent, or Firm—Schiller & Pandiscio

[57] ABSTRACT

A method and apparatus for fluorescent immunoassay utilizes total internal reflection at the interface between a solid phase and a liquid phase of lower index of refraction to produce an evanescent wave in the liquid phase. The solid phase is arranged and illuminated so as to provide multiple total internal reflections at the interface. In a preferred embodiment, the solid phase is in the form of an optical fiber to which is immobilized a component of the complex formed in the immunochemical reaction. A fluorophore is attached to another component of the complex. The fluorescent labelled component may be either the complement to or an analog of the immobilized component, depending on whether competitive or sandwich assays are to be performed. In the case of competitive assays, the labelled component is preferably pre-loaded to the immobilized component in a controlled concentration. The fiber (and the attached constituent of the assay) is immersed in the liquid phase sample. The evanescent wave is used to excite fluorescence in the liquid phase, and that fluorescence which tunnels back into the solid phase and accumulates during multiple reflections while channeled in the solid phase is detected. Diffusional preconcentration onto the reactive surface and double passing enhance the signal and signal/background ratio.

12 Claims, 2 Drawing Figures

APPARATUS INCLUDING OPTICAL FIBER FOR FLUORESCENCE IMMUNOASSAY

This application is a continuation-in-part of copending application Ser. No. 388,193, filed June 14, 1982, now abandoned.

BACKGROUND OF THE INVENTION

This invention relates to immunoassays, and more particularly to such assays wherein a fluorescent tag capable of emitting fluorescent radiation when excited by more energetic exciting radiation is incorporated into a constituent of an antigen-antibody or similar complex.

Immunoassays, in which aliquots of sample and one or more reagents are variously reacted to form antigen-antibody or similar complexes which may then be observed in order to assay the sample for the presence and titer of a predetermined moiety of the complex, are well known. Typical of such assays are those wherein a specific antibody is used to measure the quantity of the antigen for which it is specific (or vice versa). However, the technique has been extended to quantitate haptens (including hormones, alkaloids, steroids, and the like) as well as antigens, and antibody fragments (i.e., Fab) as well as complete antibodies, and it is in this broader sense that the present invention should be understood.

Sensitive immunoassays employ tracer techniques wherein a tagged constituent of the complex is incorporated into the reagent, the non-complexed tagged reagent being separated from the complexed reagent, and the complex (or non-complexed reagent) then quantitated by observing the tag. Both radioisotopes and fluorescent markers have been used to tag constituents of immunoassay reagents, the tag being respectively observed by a gamma ray counter of a fluorometer. The present invention is, however, directed only to those assays which rely on fluorescence.

The separation of the non-complexed tagged moiety from the complexed is commonly accomplished by immobilizing a predetermined one of the components of the complex to a solid phase (such as the inside wall of a test tube, glass or polymeric beads, or the like) in such a way as not to hinder the component's reactivity in forming the complex. As an example, an antibody such as immunoglobulin G (IgG) may be bound by its carboxyl terminations to a solid phase, such as glass, by a silyl compound such as 3-aminopropyltrimethoxysilane, thereby leaving the antibody's antigen reactive amino terminations free. Any complex formed incorporating the immobilized component may then be physically separated from the non-reacted complement remaining in solution, as by aspirating or decanting the fluid from a tube or eluting the fluid through a particulate bed.

In competitive immunoassay, the reagent consists of a known quantity of tagged complement (such as antigen) to the immobilized component of the complex (in this instance, antibody). The reagent is mixed with a fixed quantity of the sample containing the untagged complement to be quantitated. Both tagged and untagged complement attach to the immobolized component of the complex in proportion to their relative concentrations. After incubation for a set time, the fluid sample and reagent are separated. The complex immobilized to the solid phase is then illuminated with radiation of a wavelength chosen to excite fluorescence of the tag, and the fluorescence is measured. The intensity of the fluorescence of the immobilized complex is inversely proportional to the concentration of the untagged complement being assayed.

Alternatively, an assay may be made by immobilizing a quantity of an analog of the moiety to be quantitated (i.e., a substance which is immunologically similarly reactive) and reacting the sample with a known quantity of tagged complement. The tagged complement complexes with both the unknown quantity of the moiety in the sample and the immobilized analog. Again, the intensity of fluorescence of the immobilized complex is inversely proportional to the concentration of the (free) moiety being quantitated.

So-called "sandwich" immunoassays may be performed for multivalent complements to the immobilized component, the attached complement being then further reacted with a tagged analog of the immobilized component. Thus, bivalent antigen may be bound to an immobilized antibody and then reacted with a fluorescent tagged antibody, forming an antibody- antigen-tagged antibody sandwich that may then be separated from the unreacted tagged antibody. The intensity of the fluorescence of thus formed immobilized complex is directly proportional to the concentration of the species being quantitated.

In any of these assays, physical separation of the immobilized complex and the unreacted tagged component is required, and typical prior art methods accomplish this by aspirating, decanting, eluting, or otherwise separating the solid phase and the fluid. Beyond permitting quantitation of the reacted tagged component, such a separation step also reduces the amount of background fluorescence, an important consideration in view of the intrinsic fluorescence of substances which may be anticipated to be present in biological samples (e.g., serum biliriun, tryptophan, various drugs, and the like). Aside from requiring an additional (the separation) step in the laboratory protocol, such procedures determine a reaction end-point, and are therefore not convenient for studies of reaction dynamics.

Beyond actually removing fluid from the solid phase immobilized complex, as is common in separation immunosasays, the separation may be accomplished in situ by restricting fluorescence measurements to the immediate vicinity of the solid phase. Thus, if fluorescence is induced only within molecular dimensions of the surface of the solid phase, only those fluorophores within such a distance, and presumably therefore complexed with the immobilized component, will be excited. A method for inducing and observing fluorescence of a sample at an interface between the sample and another material has been developed by Hirschfeld (U.S. Pat. No. 3,604,927). In this method, the sample is contacted to the face of a prism, and the prism is illuminated with the exciting radiation such that total internal reflection occurs at the face contacting the sample. The sample is thus illuminated by an evanescent wave which penetrates into the sample only a relatively short distance, its electric field amplitude exponentially decreasing with distance from the interface to $e^{-1}$ of its surface value typically in less than 1000 Angstroms, the exact effective penetration depth depending upon wavelength, refractive index mismatch, and ray path relative to the critical angle. In this way, a thin surface layer of a sample may be probed. Observations of the fluorescence emitted from this lamina at large angles to the interface effectively filters the exciting radiation from the fluorescent signal.

This procedure has been specifically applied to fluorescent immunoassay by Kronick and Little (U.S. Pat. No. 3,939,350), who teach immobilizing a component of the complex to the prism (or a slide in optical contact with the prism) and observing the fluorescence of those fluorophores excited by the evanescent wave. To the extent that these are fluorophores concentrated by and bound to the immobilized component of the antigen-antibody complex, the method enhances the desired signal relative to the background fluorescence of the sample or reagent. An advantage to this approach is that the intensity of fluorescence may be observed in situ as a function of time, in contrast to separation techniques wherein the solid and liquid phases are separated before measurement, and wherein therefore an endpoint (corresponding to the time at which the separation was effected) is observed. Unfortunately, the technique only isolates a lamina no thinner than several hundred Angstroms, thereby not totally supressing intrinsic fluorescence of the sample nor completely separating bound from unbound reagent. It thus suffers a disadvantage in comparison to the previously described techniques when large intrinsic fluorescence is present or very low titers are to be quantitated.

Further, Kronick and Little's method and apparatus, in common with the wall-coated tubes of prior art fluorescent assays, observes the Lambertian radiation of a fluorescent surface. Efficient utilization of such a source requires a system having a large optical throughput (i.e., a large solid angle—aperture product). Such systems are inherently larger, more complex, and more expensive than systems having smaller throughput. For instance, throughput matching of a radiation detector to such an extended diffuse source requires a large area (and therefore, a more expensive and noisier) detector, generally used in conjunction with large collection optics. The alternative to efficient utilization of the emitted radiation is a loss in system sensitivity.

To compensate for the loss in system sensitivity brought about by poor optical throughput matching of an extended fluorescent source, one may resort to more intense excitation sources and multiple reuse of the excitation radiation by repeatedly reflecting it onto the sample. This, too, is exacerbated by the extent of the area to be illuminated and the need to throughput match the excitation source to the area. Lacking such a match, very intense (and usually complex and expensive) sources are required. Thus, the preferred embodiment of Kronick and Little (U.S. Pat. No. 3,939,350) incorporates a helium-cadmium laser and has a sensitivity sufficient only for the assay of relatively concentrated samples.

An alternative is to more heavily load the tagged component with a (generally already) highly efficient fluorophore. This commonly leads to a degradation in the specificity and avidity of the labelled component for its complement, as well as a reduction in the fluorescence efficiency, which eventually becomes limiting.

OBJECTS OF THE INVENTION

Accordingly, it is an object of the present invention to provide a method and apparatus for fluorescent immunoassay in which the fluoresent measurements may be conducted, without separating the liquid and solid phases, by observing thinner lamina than prior art total reflection fluorescence, thereby improving the rejection of intrinsic and unreacted-reagent fluorescence.

Another object of the present invention is to provide immunoassay apparatus and methods wherein the fluorescent emission may be more readily throughput matched to the opto-electronic detection system.

It is another object of the present invention to provide such a fluorescent immunoassay method and apparatus in which a low power excitation source may be efficiently optically coupled to a significant volume of the reacted sample and reagent with maximum utilization of the available power.

BRIEF DESCRIPTION OF THE INVENTION

These and other objects are met in the present invention of an immunoassay apparatus and method in which total internal reflection at the interface between a solid phase and a fluid phase of lower index of refraction is utilized to produce an evanescent wave in the fluid phase, and the fluorescence excited by the wave is observed within the "darkness cone" (i.e., at angles greater than the critical angle) by total reflection in the solid medium. The solid phase is arranged and illuminated so as to provide multiple total internal reflections at the interface. In a preferred embodiment, the solid phase is in the form of an optical fiber to which is immobilized a component or constituent of the complex formed in the immunochemical reaction. A fluorophore is attached to another component of the complex. The fluorescent labelled component may be either the complement to or an analog of the immobilized component, depending on whether competitive or sandwich assays are to be performed. In the case of competitive assays, the labelled component is preferably pre-loaded to the immobilized component in a controlled concentration. The fiber (and the attached constituent of the assay) is immersed in the fluid phase sample. The evanescent wave is used to excite fluorescence in the fluid phase, and that fluorescence which tunnels back into the solid phase (propagating within the solid phase in directions greater than the critical angle) is detected.

The observed volume is restricted not only by the rapid decay of the evanescent wave as a function of distance from the interface, but by the equally fast decrease with distance of the efficiency of tunneling, the more distant fluorophores not only being less intensely excited, and therefore fluorescing less, but their radiation less efficiently coupling into the fiber as well. As a result, the effective depth of the sensed layer is much reduced compared to the zone observed by total reflection fluorescence alone, the the coupling efficiency effectively scaling down the zone.

Multiple total internal reflections in the solid phase allow the illuminating beam to repeatedly excite an evanescent wave, thereby more efficiently coupling a small excitation source to the sample volume. This also increases the sampled volume and thus the amount of samle sensed, which is further enhanced by the diffusive circulation of sample past the surface (to which it sticks by reaction as it passes). Diffusion thus makes the actually sampled layer thickness much larger than the thin surface layer that is all that contributes to the background.

All of the radiation that tunnels back into the fiber is within the total reflection angle, and is thus trapped within the fiber. The power available from the fluorescence increases as the length of the fiber within the fluorescing material increases, however, the optical thoughput of the system (determined by the aperture [cross-section] and numerical aperture [acceptance angle] of the fiber) remains constant. The total fluorescent signal coming from the entire area of the fiber, multiplied by the increase in sampled volume due to diffusion, thus becomes available in a very bright spot, the actual cross-section of the fiber, exiting the fiber through a restricted angle determined by the critical angle of refraction within the fiber. Such a signal is easily collected at high efficiency and throughput matched to a small detector.

The signal is enhanced further because angular interference effects in the near-surface emission cause tunneling to be favored in the spatial distribution of the emission. The well known radiation field enhancement of total reflection (Hirschfeld, U.S. Pat. No. 3,604,927) also helps here, as does the opportunity of doubling both the excitation and collection efficiencies by double-passing the fiber by retroreflection.

Other objects of the invention will in part be obvious and will in part appear hereinafter. The invention accordingly comprises the apparatus possessing the construction, combination of elements, and arrangement of parts which are exemplified in the following detailed disclosure and the several steps and the relation of one or more of such steps with respect to each of the others and the scope of the application of which will be indicated in the claims.

BRIEF DESCRIPTION OF THE DRAWINGS

For a fuller understanding of the nature and objects of the present invention, reference should be had to the following detailed description taken in connection with the accompanying drawings wherein.

In the figures, like index numbers refer to like elements.

DETAILED DESCRIPTION

Figure 1:
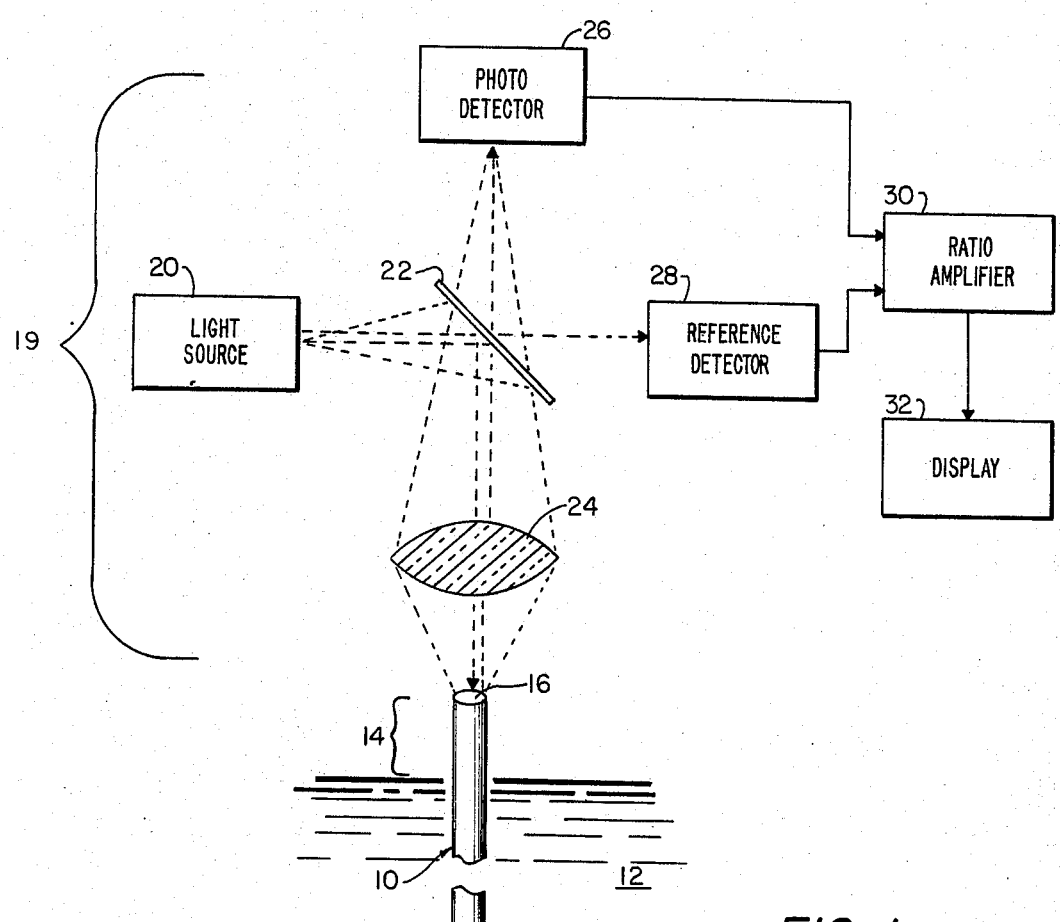
FIG. 1 is a schematic view of an exemplary immunoassay device embodying the principles of the present invention.

As is well known, when a wave front of electromagnetic radiation propagating through a medium of a given refractive index, $n_1$, arrives at the interface between that medium and another medium of refractive index $n_2$, refraction occurs, the wave front being deflected in accordance with Snell's law, $$n_1 \sin i = n_2 \sin r, \quad (1)$$

where i and r are the angles the normal to the interface makes with the normals to the wave front respectively before and after the passage of the wave front through the interface. If $n_1$ is greater than $n_2$, sin r will become unity for some value of i less than 90°. For values of the angle of incidence i greater than this critical angle, normal refraction no longer occurs at the interface, the wave front instead being reflected back into the first medium. This phenomenon, known as total internal reflection, is well known, and is, for instance, the principle upon which optical fiber light pipes depend, these being provided with walls configured so as to support multiple total internal reflections.

Even for values of the incidence angle i equal to or greater than the critical angle, refraction does, in fact, occur, although in the simplest case there is no net transport of energy into the low index medium. Rather, at each point on the interface there is a periodic flow of energy across the interface, the energy transported into the low index medium being equal to that transported back. The resulting wave in the lower index medium is a so-called evanescent wave of the same wavelength as the incident wave, propagating parallel to the interface at a velocity matching the projected velocity of the incident wavefront, and having an amplitude which is greatest at the interface and which decays exponentially with distance from the interface, becoming sensibly zero at distances large compared to the wavelength.

The simplest case of total internal reflection is that of a nonabsorbent non-emitting low index medium. In this case, no energy is lost to or gained from the low index medium by the evanescent wave, the energy transported from one medium to the other exactly balancing that transported back. Consequently, the reflection at the interface is, in effect, total. If, however, the lower index medium is absorbent, some of the energy will be extracted from the evanescent wave, and therefore will not be returned to the higher index medium. The reflection at the interface is no longer really total. This phenomenon, known as attenuated total reflection (ATR), was first applied to absorption spectroscopy in 1959 by Fahrenfort, who measured the energy in the reflected beam to determine the extent of absorption by a sample forming the low index medium. If the absorbing species is fluorescent, the evanescent wave may be used to induce fluorescence. This phenomenon, known as total reflection fluorescence (TRF), is the subject matter of Hirschfeld's U.S. Pat. No. 3,604,927. Both ATR and TRF have been extensively employed in the study of surface effects, the limited amplitude of the evanescent wave at fractional wavelength distances from the interface effectively delimiting the observed sample thickness.

Detailed consideration of the phenomonenon also indicates that a wave emanating from the lower index medium in the immediate vicinity of the interface will, in part, be refracted into the higher index medium at an angle greater than the critical angle. This phenomenon is known as tunnelling, and this radiation may also be propagated within the high index medium by total internal reflection, provided the medium is appropriately configured.

The present invention relies on both TRF and tunnelling of the fluorescence with multiple internal reflections of both exciting and fluorescent radiation.

Referring to FIG. 1, there may be seen, partially in schematic view, the essential elements of a preferred embodiment of the present invention. An optical fiber, indicated in general by index numeral 10 and shown only in part, is immersed in a fluid sample, generally indicated by the numeral 12. Fiber 10 is an elongate substantially cylindrical optically transparent body adapted to propagate along its length through multiple total internal reflections optical radiation entering an end of the fiber within an established solid angle substantially rotationally symmetric about the fiber's axis. As is well known in the art of fiber optics, the maximum acceptance angle, with regard to the fiber axis, B, for the radiation entering the fiber and so propagated within it, is established by the refractive indices of the fiber and the surrounding medium. For radiation initially propagating through a medium of refractive index $n_o$, incident upon a fiber of refractive index $n_1$ otherwise surrounded by a material of refractive index $n_2$, the maximum acceptance angle may be found from the equation $$N.A. = n_o \sin B = (n_1^2 = n_2^2)^{\frac{1}{2}}, \quad (2)$$

where N.A. is the so-called numerical aperture of the fiber. By way of example, but not limitation, fiber 10 may be any of a number of optically transparent materials, such as glass, quartz, polyolefin, nylon, or the like, chosen to have an index of refraction greater than that of fluid 12 (typically, an aqueous solution having an index of refraction near 1.33 or a serum sample having an index of refraction near 1.35) and further chosen to be relatively insoluble and nonreactive with the fluid. Whole other fiber diameters may be used, it has been found that 200 microns is satisfactory. For most assays, a fiber 25 mm in length appears adequate, however it will be understood that the length of the fiber can be accommodated to the assay to be undertaken.

As will be described in detail hereinafter, fiber 10 is provided with a surface coating including means for attaching selected moieties of an antigen-antibody complex (as herein used, "antigen-antibody complex" includes complexes not only of complete antibodies and antigens, but complexes incorporating the immunologically reactive fragments of either of both).

Fluid 12 comprises the sample or reagent, as will be described hereinafter in greater detail.

Preferably, fiber 10 is supported in fluid 12 by any of a number of mechanical means (not shown) so as to expose all but an end portion 14 of the fiber to the fluid, leaving the polished end face 16 of end portion 14 optically unobscured by fluid or holder. Thus, fluid 12 may be confined in an open-ended upright container and end portion 14 of fiber 10 led through and affixed to a removable cap. Then too, fluid 12 may be completely enclosed and fiber 10 led through a wall of the enclosure. Inasmuch as neither the container for fluid 12 nor the holder for fiber 10 is a critical element of the invention, they are omitted from the drawing for the sake of clarity. Fiber 10 is supported within the fluid so as to insure, with the exception of end portion 14, the fiber does not contact the walls of the enclosure or the support means. It will be understood by those skilled in the art of optical fibers that end portion 14 is provided with a means, such as cladding (not shown) to insure isolation of the energy within the fiber from any perturbations due to the support means or enclosure.

Polished end face 16 is preferably planar and disposed normal to the axis of fiber 10. Optionally, the end face 17 of the fiber distal from end face 16 is also polished flat normal to the axis of the fiber and further provided with a mirror coating 18 (or a separate mirror) to cause radiation trapped in the fiber to double pass the fiber.

Fiber 10 is intended for use with fluorometer 19. Fluorometer 19 comprises light source 20, dichroic mirror 22, objective 24, photodetector 26, reference detector 28, ratio amplifier 30, and display 32.

Light source 20 provides optical radiation of the appropriate frequency, chosen on the basis of the fluorophore used as the tag in the assay of interest, to excite fluorescence in the tagged component of the reagent. Light source 20 preferably provides this radiation over only a narrow wavelength band, chosen to maximize the fluorescence. Hence, light source 20 typically includes, in addition to the preferred tungsten-halogen lamp and associated power supply, a band-pass filter. Alternatively, it will be understood light source 20 might incorporate other sources, such as a mercury lamp, flash lamp, or a laser. Light source 20 also includes an appropriate beam shaping aperture and optics, as will be understood by those skilled in the art, to illuminate objective 24 with a beam of the appropriate vergence so as to permit the objective to image the source aperture on end face 16 of fiber 10 with no ray incident on the end face at an angle of incidence greater than that corresponding to the numerical aperture of the fiber.

Interposed between light source 20 and objective 24 is dichroic beamsplitter 22. In the preferred embodiment, beamsplitter 22 is a low-pass interference filter with a cut-off frequency chosen to be between the frequencies of maximum absorption and maximum fluorescence emission of the fluorophore of interest. Beamsplitter 22 thus reflects the high frequency (short wavelength) fluorescence exciting radiation from light source 20 and transmits the low frequency radiation corresponding to the fluorescence maximum of the fluorophore.

Objective 24 is selected to image light source 20 on end face 16 of fiber 10, so as to just fill the end face with an image of the beam shaping aperture of the source, the maximum angle of incidence of a ray being selected to be less than that corresponding to the numerical aperture of the fiber. Objective 24 is also selected so as to collect substantially all of the radiation exiting end face 16 over the numerical aperture of the fiber and image the end face at photodetector 26.

Photodetector 26 is positioned to receive, through beamsplitter 22, an image of end face 16 of fiber 10 projected toward the photodetector by objective 24. Photodetector 26 preferably includes a photomultiplier (provided with appropriate power supply and field optics to restrict the detector's field of view to end face 16, as is well known in the art), chosen to have maximum sensitivity in the region of peak fluorescence of the fluorophore. Photodetector 26 is further preferably provided with a blocking filter corresponding to the band-pass filter provided light source 20.

Reference detector 28, preferably a photodiode, is disposed to intercept radiation from light source 20 passing through dichroic beamsplitter 22. Reference detector 28 is chosen for peak sensitivity in the spectral region of light source 20 passed by dichroic beamsplitter 22, and includes appropriate field stops and optics to limit its field of view to the source.

Ratio amplifier 30 is any of a number of well-known electronic means providing an output signal which is proportional to the ratio of a pair of input signals, so connected to the outputs of photodetector 26 and reference detector 28 as to provide a signal proportional to the ratio of the output of the photodetector to that of the reference detector. For instance, ratio amplifier 30 may be a variable gain amplifier amplifying the output from photodetector 26 and having a gain inversely proportional to the output from reference detector 28.

The output of ratio amplifier 30 is connected to and serves as the input for display 32. Display 32 is any of a number of devices that provides a visual signal proportional to an electrical input, and may be, for instance, a meter, a digital display, a strip chart recorder, or the like.

Figure 2:
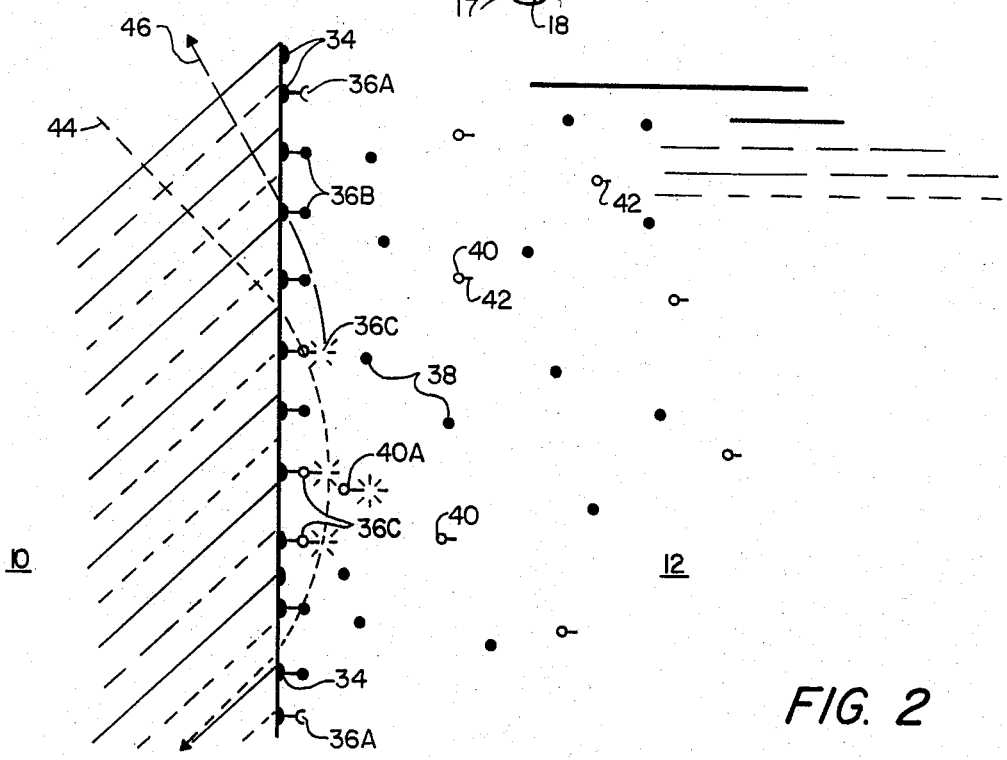
FIG. 2 is a stylized view of a portion of the device of FIG. 1 illustrating a typical immunochemical reaction and radiation energy paths of interest in the realization of the invention.

Turning now to FIG. 2, there may be seen a highly stylized representation of a longitudinal cross-sectional portion of fiber 10 and the adjacent fluid 12.

The surface of fiber 10 is provided with a plurality of coupling sites 34, to most of which are bound a moiety 36 of the antibody-antigen complex. (As used herein, the phrase "moiety of an antibody-antigen complex" refers to an immunologically reactive portion of such a complex, and includes haptens as well as complete antigens and antigen reactive antibody fragments [Fab] as well as complete antibodies). Coupling sites 34 are so selected as to immobilize moieties 36 without appreciably affecting the reactivity (e.g., the affinity and avidity) of the moiety for the complementary portion of the complex. In a preferred embodiment, fiber 10 is of glass or quartz, coupling sites 34 are the reactive groups of a silyl compound such as 3-aminopropyltrimethoxysilane, and moieties 36 are an antibody such as immumoglobulin G (IgG). As noted hereinabove, for this particular combination of solid phase, coupling site 34 and moiety 36 may be bound through the antibody's carboxyl terminations, thereby leaving the antibody's antigen reactive amino terminations free. The method for preparing the glass surface of fiber 10, of attaching the silyl compound thereto, and of covalently bonding an antibody to the glass through the silyl coupling, are described be Weetall (U.S. Pat. No. 3,652,761), where may also be found a description of other silyl compounds and the methods by which carboxyl, amino, and other reactive groups of antibody or antigen (or their fragments) may be covalently bound to various inorganic materials. It should be noted that an extensive art for immobilizing antigens or antibodies to polymers also exists, and those skilled in the art will understand that coupling sites 34 for antigen or antibody might be provided on polymeric fibers also. Thus, for instance, if fiber 10 is of nylon (polyamide), the coupling may be in the form of the substitution of an appropriate radical for the hydrogen bound to either the carbon or nitrogen of the molecular chain.

It should be noted that coupling sites 34 may also incorporate spacer groups, as are well known in the art, to insure sufficient separation between fiber 10 and moieties 36 as to minimize steric hindrance of the antibody-antigen binding process. For example, coupling sites 34 might include a polyethylene chain, as for example in the case of 1,6 diaminohexane or 6 aminohexanoic acid bound to fiber 10 through a peptide bond and respectively providing a free primary amino and a free carboxyl group for covalently binding to the carboxyl or amino termination of a protein moiety 36. Either of these coupling materials provide a 6-carbon chain between terminations, thereby spacing moiety 36 from fiber 10 by the corresponding distance. Similar appropriate coupling and spacer materials are well known in the arts of both immunoassay and affinity chromatography.

In a preferred embodiment, fiber 10 is provided with moiety 36 having unoccupied binding sites, as indicated at index numerals 36A, although it will be understood that the moiety might in part be provided with attached tagged complement for competitive immunoassays, if desired. Thus, in one embodiment moiety 36 is an antibody, and a preloading of tagged antigen or hapten might be incorporated.

Fluid 12 is preferably a buffered aqueous solution containing, inter alia, the component 38 of the particular antibody-antigen complex to be quantitated and (unless it is provided initially complexed to a portion of moiety 36 on fiber 10) a known titre of tagged component 40. For the preferred embodiment so far described, component 38 and tagged component 40 are similar antigens or haptens. For optimum immunological reactions, the fluid is buffered in the range of pH 6-9, and preferably in the range pH 7-8. To this end, various buffers, such as borate, tris, carbonate, and the like may be employed.

Each of the tagged components 40 is provided with a pre-determined quantity of fluorophore 42, thereby providing a tag. The particular fluorescing compounds of interest for tagging include fluoresceine, tetramethylrhodamine, rare earth chelates, and the like. Methods for linking fluorescent tags to proteins are well known in the art, and many of the commercially available fluorescing compounds have groups for linking to proteins.

When fiber 10 and fluid 12 as above described are brought into contact, components 38 and tagged components 40 in the fluid react with moieties 36 bound to the fiber. To the extent that components 38 and 40 are similarly reactive with moieties 36, they will form immunological complexes with the moieties in direct proportion to their respective concentrations, as indicated by index numbers 36B and 36C.

Also indicated in FIG. 2 is the path 44 of the optical energy in a totally reflected wavefront at one instant in time. Those fluorophores 42 in the vicinity of this path are in the evanescent wave, and will consequently fluoresce, provided the wavelength of the wavefront is appropriate. As depicted, the fluorophores of the tagged components complexed with moieties 36 (as at 36C) are within the evanescent wave and consequently fluoresce. It will be noted that non-complexed tagged components 40 (such as at index number 40A) sufficiently close to the fiber are also excited by the evanescent wave, while those further from the fiber are not.

While the radiation emitted by the fluorescing components may be in any direction, for many of the fluorescing complexes 36C some of the emitted radiation tunnels back into the fiber, as shown by ray 46. As seen from the fluorescing particle, only some 2% of the total solid angle about the particle is collected by the return beam. However, because of angular interference due to fluorescent emission near the fiber-fluid interface, this represents typically better than 10% of the fluorescent radiation. As tunnelling results in a ray path in the fiber at or above the critical angle (the angular interference effects favoring paths slightly greater than the critical angle), ray 46 will be multiply totally reflected along the fiber, propagating along the fiber toward the ends of the fiber. A portion of the fluorescent radiation tunnelling into to the fiber thus exits end face 16 (FIG. 1). If a mirror is provided at end face 17, all of the radiation tunnelling into the fiber (less absorption and reflection losses) exits end face 16. As the numerical aperture of a fiber is defined in terms of the largest solid angle outside the fiber end face that will result in total internal reflection within the fiber, and as objective 24 has been chosen to collect this angle, half or more of the fluorescent radiation tunnelling into the fiber from the tagged components complexed with moieties 36 attached to the fiber (less losses in the fiber) will be collected by objective 24.

It should be particularly noted that the geometry of fiber 10, unlike that of an ATR plate or prism, is particularly adapted to allow throughput matching of the fiber to other optical components. The cylindrical form of the fiber confines the radiation propagating within it to propagate within a fixed rotationally symmetric solid angle and to pass into and out of the fiber through small circular apertures. Both the size and symmetry of the radiation pattern are easily throughput matched to conventional optical systems. In contrast, a prism or a plate permits the energy propagating within to fan out in at least one dimension, resulting in a radiation pattern which is difficult to throughput match, having as it does both a large spatial extent and a large divergence in at least one dimension.

An additional advantage of the geometry of fiber 10 as compared to that of an ATR plate or prism is in the efficiency of the fiber as a concentrator in what is a diffusion process. In this regard, it should be noted that formation of the antibody-antigen complex is dependent upon the diffusion of the unbound component(s). For a given mean diffusion thickness (i.e., a given thickness of the layer of sample scavenged by diffusion in a given time), a greater sample volume is scavenged by a small diameter cylindrical surface (the fiber) than is by an plane surface (the plate or prism) of equal area. Thus, the fiber more rapidly concentrates a given titer of unbound constituent of the complex to the immobilized constituent than does the plate or prism.

In operation, radiation of a wavelength chosen to excite fluorescence in fluorophores 42 is supplied by light source 20, via dichroic beamsplitter 22 and objective 24, so as to illuminate end face 16 of fiber 10 within the cone angle defined by the numerical aperture of the fiber. This radiation is consequently propagated within fiber 10 at or above the critical angle, multiply totally internally reflecting along the length of the fiber and producing an evanescent wave in fluid 12 adjacent the fiber. Competitive binding of tagged components 40 and untagged components 38 to moieties 36 attached to the fiber results in fluorescently tagged complexes 36C in proportion to the relative concentration of tagged to untagged components. Excited by the evanescent wave, the tagged complexes 36C fluoresce. A portion of the fluorescent emission tunnels into the fiber, and one-half or more of this exits the fiber at end face 16, where it is collected by objective 24 and projected toward photodetector 26. As fluorescence occurs at longer wavelengths (lower frequencies) than the exciting radiation, the low-pass dichroic beamsplitter 20 allows this radiation to pass to the photodetector, which in turn provides an electrical signal proportional to the intensity of the fluorescence. Dichroic beamsplitter 22 also allows some radiation from source 20 to illuminate reference detector 28, which provides an electrical signal proportional to the source intensity. These two electrical signals are ratioed by ratio amplifier 30, to provide an electrical output signal proportional to fluorescent intensity corrected for source intensity variations, which is displayed by display 32.

It will be appreciated that various modifications may be made to the apparatus and method without departing from the principles of the invention. For instance, as already noted, competition assay kits may be provided with a pre-established loading of tagged constituent complexed to the immobilized moiety. Clearly, the apparatus may be adapted for sandwich assays as well as competitive assays. Also, the moiety secured to the fiber need not be an antibody, but may instead be the active fragment (Fab) of an antibody, or it may be antigen or a hapten. Then, too, fiber 10 may be provided without an affixed component of the antigen-antibody complex, but with merely a coating of coupling sites 34, in order that the user may custom-tailor assays. Further, multiple assays may be provided on the same fiber, the individual assays using fluorescent materials of differing fluorescent properties. As further noted hereinabove, fiber 10 may be provided a reflecting end face 17 distal end face 16, to cause multiple passes of the exciting beam and allow collection of all the tunnelling fluorescent radiation.

It will also be apparent to those skilled in the art that focal isolation, or a coherent source and spatial filtering, rather than a beam splitter, may be used to separate the exciting and fluorescent radiation in fluorometer 18. Thus, if laser illumination is employed, the exciting radiation may be made much more slowing vergent than is the fiber acceptance angle, while the fluorescent radiation tunnelling into the fiber will exit the fiber end face with a divergence up to the acceptance angle.

Additionally, light source 20 may be provided with multiple emission bands, and a multiplicity of photodetectors 26 may be provided, each simultaneously observing a different spectral bandpass.

While a preferred embodiment of fluid 10 is a buffered aqueous solution, it will be understood that other fluids, as appropriate, may be substituted. Thus, fluid 10 may be any biological fluid, an environmental specimen fluid, or the like. Then, too, while the method and apparatus are particularly suited for in situ observations of dynamic processes, it will be understood that the fiber could be removed from the sample fluid for observation.

Since these and certain other changes may be made in the above apparatus and method without departing from the scope of the invention herein involved, it is intended that all matter contained in the above description or shown in the accompanying drawing shall be interpreted in an illustrative and not a limiting sense.

What is claimed is:

1. Apparatus for fluorescence immunoassays relying on an immunochemical complex formed by reaction between a first constituent of said immunochemical complex and a second constituent of said immunochemical complex, which second constituent includes a fluorescent tag, said apparatus comprising in combination:
    an optical fiber transmissive to radiation which can excite fluorescene of said fluorescent tag and transmissive to fluorescent radiation from said fluorescent tag; and
    a plurality of said first constituents so attached to at least a portion of the side surface of said optical fiber as to leave substantially unaffected the reactivity of said first constituent to form said immunochemical complex, with at least a part of said first constituent being complexed with a predetermined amount of said second constituent.

2. Apparatus for fluorescence immunoassays relying on an immunochemical complex formed by a reaction between a first constituent of said immunochemical complex and a second constituent of said immunochemical complex, which second constituent includes a fluorescent tag, said apparatus comprising in combination:
    a radiation source capable of producing radiation having a first spectral energy distribution that can excite fluorescence in said fluorescent tag;
    an optical fiber transmissive to radiation having said first spectral energy distribution and further being transmissive to radiation having a second spectral energy distribution corresponding to the fluorescence of said fluorescent tag;

means for injecting radiation of said first spectral energy distribution from said source into one end of said optical fiber;

means on said optical fiber for so attaching a plurality of said first constituents to the side surface of said fiber as to leave substantially unaffected the reactivity of said first constituent to form said immunochemical complex; and means for detecting radiation of said second spectral energy distribution propagating within said fiber.

3. Apparatus as claimed in claim 2 wherein said means for attaching comprises a coating reactive with said plurality of first constituents.

4. Apparatus as claimed in claim 2 including a plurality of said first constituents attached to at least a portion of said side surface of said optical fiber by said means for attaching.

5. Apparatus as claimed in claim 4 wherein at least part of first constitutents are complexed with a predetermined amount of said constituents incorporating a fluorescent tag.

6. Apparatus as claimed in claim 4 wherein said first constitutents are antibodies.

7. Apparatus as claimed in claim 4 wherein said first constitutents are antigen-reactive antibody fragments.

8. Apparatus as claimed in claim 4 wherein said first constitutents are antigens.

9. Apparatus as claimed in claim 4 wherein said first constitutents are haptens.

10. Apparatus as defined in claim 2 wherein said means for detecting radiation is disposed for detecting said radiation of said first spectral energy exiting from said one end of said optical fiber.

11. In an immunoassay relying on a constituent of an immunochemical complex wherein said constituent includes a fluorescent tag, the improvement comprising:

immersing in a sample to be assayed an optical fiber transmissive to excitation radiation that can excite fluorescence of said tag and transmissive to fluorescent radiation from said tag, said optical fiber having selected constituents of said immunochemical complex attached to its surface for forming said immunochemical complex with said sample;

illuminating at least one end of said optical fiber with said excitation radiation so as to excite fluorescence of said fluorescent tag in said immunochemical complex attached to said optical fiber, said excitation radiation being supplied to said one end of said optical fiber over a solid angle equal to or smaller than that defined by the numerical aperture of said optical fiber so that said excitation radiation propagates within said optical fiber along paths substantially above the critical angle with regard to the side surface of said optical fiber;

collecting over a similar limited solid angle fluorescent radiation that arises from the excitation of said fluorescent tag in said immunochemical complex attached to said optical fiber and that exits from an end of said fiber; and measuring the intensity of said fluorescent radiation exiting from said optical fiber.

12. The immunoassay as set forth in cliam 11 wherein said step of collecting is with respect to said fluorescent radiation exiting from said one end.

* * * * *